United States Patent
Geissler et al.

(10) Patent No.: US 6,348,603 B1
(45) Date of Patent: Feb. 19, 2002

(54) PROCESS FOR THE PREPARATION OF ISOCHROMAN-3-ONES

(75) Inventors: Holger Geissler, Mainz; Ralf Pfirmann, Griesheim, both of (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/668,915

(22) Filed: Sep. 25, 2000

(30) Foreign Application Priority Data

Sep. 23, 1999 (DE) .......................................... 199 45 561

(51) Int. Cl.$^7$ ........................................... C07D 407/00
(52) U.S. Cl. ...................................................... 549/280
(58) Field of Search .................................... 549/280

(56) References Cited

FOREIGN PATENT DOCUMENTS

| EP | 0 834 497 | 4/1998 | |
|---|---|---|---|
| WO | WO 97/00850 | 1/1997 | |
| WO | WO 97/12864 | 4/1997 | |
| WO | WO 00/17186 | 3/2000 | ................. 549/280 |

OTHER PUBLICATIONS

Yamamoto, Akio et al., Tetrahedron Letters, vol. 38, No. 21, "Palladium–catalyzed carbonylation of benzyl alcohol and its analogs promoted by HI in aqueous systems." pp. 3747–3750.

Stille, J. K., et al. Journal of American Chemical Society, 1980, vol. 102, "Synthesis of lactones by the palladium-–catalyzed carbonylation of halo alcohols." pp. 4193–4198.

Holleman–Wiberg, Lehrbuch der anorganichen chemie, 91–100, Auflage, Verland Walter de Gruyter, Berlin 1985, pp. 246–248.

Kislina, et al., Russian Chemical Bulletin, 1994, vol. 43, "The acidity scale of HCl solutions in N, N–dimethylformamide", pp. 960–963.

Primary Examiner—Alan L. Rotman
Assistant Examiner—Raymond Covington
(74) Attorney, Agent, or Firm—Scott E. Hanf

(57) ABSTRACT

The present invention relates to a process for the preparation of an isochroman-3-one of the formula (I)

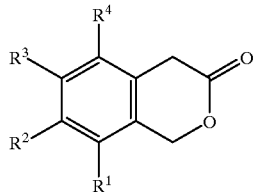

by reaction of a 1,2-bishalomethylbenzene of the formula (II)

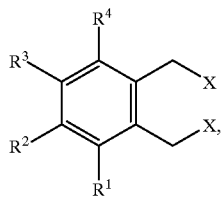

in which X is chlorine, bromine or iodine, with carbon monoxide and a compound of the formula (III)

$$R^5R^6R^7C{-}OH \quad\quad (III)$$

at a CO pressure of 0.1 to 50 MPa and a temperature of 20 to 200° C. in the presence or absence of an ionic halide, in the presence of a palladium catalyst and of a dipolar aprotic solvent, with addition of water or without addition of water, where in the formulae (I) and (II) the radicals $R^1$, $R^2$, $R^3$ and $R^4$ independently of one another are: a hydrogen or fluorine atom; an NC or $F_3C$ group; an alkyl, alkoxy or acyloxy radical, in each case having 1 to 18 carbon atoms; or a $C_6$–$C_{18}$-aryloxy, aryl or heteroaryl radical, where 1 to 3 atoms from the group consisting of O, N and/or S are present as heteroatoms; or in which at least two of the radicals $R^1$, $R^2$, $R^3$ and $R^4$ are linked to one another and form at least one aliphatic or aromatic ring having 5 to 18 carbon atoms, and in formula (III) the radicals $R^5$, $R^6$ and $R^7$ are identical or different and are a $C_1$–$C_{18}$-alkyl, an HOC(=O)—, $H_3CC(=O)CH_2$— or ($C_6$–$C_{18}$-aryl)-$CH_2$— radical or at least two of the radicals $R^5$, $R^6$ and $R^7$ are linked to one another and form at least one aliphatic or aromatic ring having 5 to 18 carbon atoms.

16 Claims, No Drawings

PROCESS FOR THE PREPARATION OF ISOCHROMAN-3-ONES

CROSS-REFERENCES TO RELATED APPLICATIONS

The present invention is described in the German priority application No. DE 19945561.9 filed Sep. 23, 1999, which is hereby incorporated by reference as is fully disclosed herein.

BACKGROUND OF THE INVENTION

The present invention relates to an advantageous process for the preparation of isochroman-3-ones.

Isochroman-3-one is of great interest as an intermediate in the synthesis of pharmaceuticals and plant protection agents.

The use of isochroman-3-one as an intermediate in the preparation of fungicides and pesticides follows, for example, from WO 97/12864.

As a rule, the quality of traditional chemical processes is defined by the space/time yield. In catalytic chemical processes, however, the catalytic turnover number (TON, i.e. the value which indicates how often a catalyst particle is used in the reaction) and the catalytic turnover frequence (TOF, i.e. the value which indicates how often a catalyst particle is used in the reaction in one hour) are generally used as quality criteria. In comparison with the space/time yield, the TON and TOF additionally give information about the quality of the catalyst employed in the reaction.

Various processes for the preparation of isochroman-3-one are known in the literature.

Thus in Tetrahedron Lett. 1997, Vol. 38, 3747 to 3750, Yamamoto describes a synthesis of isochroman-3-one by reaction of 1,2-bishydroxymethylbenzene and carbon monoxide in the presence of 1 mol % of a palladium catalyst and 10 mol % of hydrogen iodide. At 90° C. and a carbon monoxide pressure of 9 MPa in acetone/water as a solvent, isochroman-3-one is obtained in isolated form in 56% yield after a reaction time of 42 hours.

Disadvantages of this process which may be mentioned are the presence of the very corrosive hydrogen iodide and the fairly long reaction time.

In J. Am. Chem. Soc. 1980, Vol. 102, 4193 to 4198, Stille describes the synthesis of isochroman-3-one by reaction of ortho-bromomethylbenzyl alcohol, carbon monoxide and potassium carbonate in the presence of 1.6 mol % of a palladium catalyst and one drop of hydrazine in tetrahydrofuran as solvent. After 24 hours at 25° C. and a carbon monoxide pressure of 0.1 MPa, isochroman-3-one is obtained in isolated form in a yield of 71%.

It is a disadvantage that the ortho-bromomethylbenzyl alcohol needed as a starting substance is not easily accessible. Moreover, the use of potassium carbonate makes simple carrying-out of the process difficult (release of $CO_2$). Furthermore, a comparatively long reaction time has to be accepted.

A two-stage process for the preparation of isochroman-3-one derivatives follows from WO 97/00850 A1, where initially a 1,2-bishalomethylbenzene derivative of the formula (A)

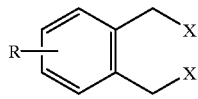

(A)

in which R is H, a halogen, a $C_1$–$C_6$-alkyl or $C_1$–$C_6$-alkoxy radical and X is a halogen, carbon monoxide and water are reacted in an organic solvent in the presence of a hydrogen halide absorbent and a catalyst and the salt of the ortho-hydroxymethylphenylacetic acid of the formula (B) occurring as an intermediate, in which M is an alkali metal or alkaline earth metal and n is 1 or 2,

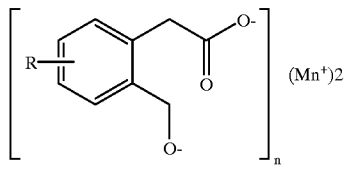

(B)

is subsequently treated with an acid and converted into the corresponding isochroman-3-one. Suitable catalysts are palladium, cobalt and iron catalysts. The hydrogen halide absorbents used can be bases, in particular inorganic bases, for example calcium hydroxide. In the second reaction stage of this process, the acid used is, for example, hydrochloric acid in order to bring about the conversion of the salt of the ortho-hydroxymethylphenylacetic acid derivative of the formula (B) into the corresponding isochroman-3-one. The maximum TOF is $153 \times h^{-1}$; TON=153; yield 76.7% (cf. Working Example 4). The maximum TON is 170 (TOF= $24 \times h^{-1}$); yield 84.7% (cf. Working Example 17).

According to this process, a yield of up to 87.4% of isochroman-3-one can indeed be achieved, but where a comparatively small amount of 8.75 g of α,αN-orthoxylylene dichloride (1,2-bischloromethylbenzene) is reacted in not less than 100 g of tert-butanol. For further work-up, the reaction mixture is treated with water, insoluble solids are removed by filtration and the filtrate is extracted several times with ether. After acidifying with concentrated hydrochloric acid, it is extracted again with ether and isochroman-3-one is obtained from the collected ether fractions (TON= 87; TOF=$4.2 \times h^{-1}$; cf. also Working Example 5).

Owing to the use of bases in the first step of the process and to the acidification in the second step, not fewer than 3 equivalents of monovalent salt are formed per equivalent of isochroman-3-one. Disadvantages in this process are, on the one hand, the use of large amounts of solvents and the formation of large amounts of salt and, on the other hand, the two-stage nature of the process and the numerous purification and extraction steps as well as the repeated use of ether as an extractant.

SUMMARY OF THE INVENTION

In view of the disadvantages of the process outlined above, the present invention is based on the object of making available a novel process for the preparation of isochroman-3-ones which, on the one hand, can be carried out with comparatively low expenditure and, on the other hand, avoids the disadvantages of the processes of the prior art described beforehand and makes the desired product accessible in good yield and high purity.

DESCRIPTION OF THE PREFERRED EMBODIMENTS

This object is achieved by a process for the preparation of an isochroman-3-one of the formula (I)

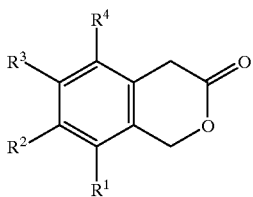

by reaction of a 1,2-bishalomethylbenzene of the formula (II)

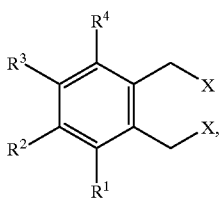

in which X is chlorine, bromine or iodine, with carbon monoxide and a compound of the formula (III)

at a CO pressure of 0.1 to 50 MPa and a temperature of 20 to 200° C. in the presence or absence of an ionic halide, in the presence of a palladium catalyst and of a dipolar aprotic solvent, with addition of water or without addition of water, where in the formulae (I) and (II) the radicals $R^1$, $R^2$, $R^3$ and $R^4$ independently of one another are:

a hydrogen or fluorine atom;

an NC or $F_3C$ group;

an alkyl, alkoxy or acyloxy radical, in each case having 1 to 18 carbon atoms; or a $C_6$–$C_{18}$-aryloxy, aryl or heteroaryl radical, where 1 to 3 atoms from the group consisting of O, N and/or S are present as heteroatoms;

or in which at least two of the radicals $R^1$, $R^2$, $R^3$ and $R^4$ are linked to one another and form at least one aliphatic or aromatic ring having 5 to 18 carbon atoms, and in formula (III) the radicals $R^5$, $R^6$ and $R^7$ are identical or different and are a $C_1$–$C_{18}$-alkyl, an HOC(=O)—, $H_3CC(=O)CH_2$— or ($C_6$–$C_{18}$-aryl)-$CH_2$— radical or at least two of the radicals $R^5$, $R^6$ and $R^7$ are linked to one another and form at least one aliphatic or aromatic ring having 5 to 18 carbon atoms.

The reaction of the 1,2-bishalomethylbenzene of the formula (II) can be described schematically—substantiated by means of a 1,2-bischloromethylbenzene as an example of a compound of the formula (II) and by means of tert-butanol as an example of a compound of the formula (III)—in simplified form by the following equation.

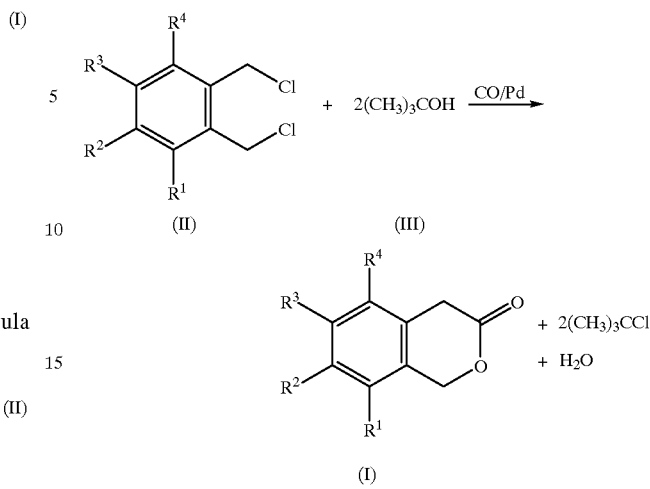

As follows from this equation which serves here as an illustrative example, the corresponding isochroman-3-one of the formula (I), tert-butyl chloride and water are formed.

The process according to the invention makes it possible to react the 1,2-bishalomethylbenzene of the formula (II) in concentrations which are significantly higher than in the process according to WO 97/00850 A1. Owing to this, the space/time yield is advantageously increased and an industrial procedure is favored to a corresponding extent.

A further advantage is that, in comparison to the process of WO 97/00850 A1, the salt of the formula (B) is not to be formed and also the salt is not obtained which is formed by the reaction of the hydrogen halide absorbent (base) with hydrogen halide. Thus, the process according to the invention proceeds in the absence of a hydrogen halide absorbent of this type and it is moreover advantageously possible to dispense with addition of acid in the second reaction step.

The radicals $R^1$, $R^2$, $R^3$ and $R^4$ are, in particular, independently of one another hydrogen, fluorine, $C_1$–$C_4$-alkyl or $C_1$–$C_4$-alkoxy or two of the radicals $R^1$, $R^2$, $R^3$ and $R^4$ are linked to one another and form an aliphatic or aromatic ring having 5 to 10 carbon atoms. Preferably, $R^1$, $R^2$, $R^3$ and $R^4$ independently of one another are hydrogen, fluorine or $C_1$–$C_4$-alkyl or $C_1$–$C_4$-alkoxy, in particular hydrogen, fluorine or $C_1$–$C_4$-alkyl.

In the formulae (I) and (II), two, three or four, in particular three or four, of the radicals $R^1$, $R^2$, $R^3$ and $R^4$ can be hydrogen.

It is possible in the process to employ a 1,2-bishalomethylbenzene of the formula (II) to good effect, in which X is chlorine or bromine, in particular chlorine.

A compound of the formula (III) is employed to good effect, in which the radicals $R^5$ $R^6$ and $R^7$ are identical or different and are a $C_1$–$C_{18}$-alkyl or ($C_6$–$C_{18}$-aryl)-$CH_2$— radical, in particular a $C_1$–$C_{12}$-alkyl radical, preferably a $C_1$–$C_8$-alkyl radical. The alkyl radical can be straight-chain or branched and is in particular straight-chain.

Of particular interest are compounds of the formula (III) in which one of the radicals $R^5$, $R^6$ and $R^7$ is a $C_1$–$C_{12}$-alkyl radical, in particular a $C_1$–$C_8$-alkyl radical, and the remaining radicals are an ethyl or methyl radical, in particular a methyl radical.

The process according to the invention is carried out particularly simply by employing tert-butanol as the compound of the formula III.

The compound of the formula (III) is employed corresponding to an amount of 0.8 to 10, in particular 0.9 to 3, preferably 1 to 2.5, mol per mole of 1,2-bishalomethylbenzene.

As mentioned at the outset, the process can be carried out in the presence or absence of an ionic halide.

Customarily, the ionic halide is an alkali metal, ammonium or phosphonium halide, in particular an alkali metal or ammonium halide, where the halide has the meaning chloride, bromine or iodide, in particular chloride or bromide, preferably chloride.

The ionic halide employed can be ammonium bromide, lithium bromide, sodium bromide, potassium bromide, tetrabutylphosphonium bromide, ammonium chloride, dimethylammonium chloride, diethanolammonium chloride, lithium chloride, sodium chloride, potassium chloride, tetrabutylphosphonium chloride, ammonium iodide, lithium iodide, sodium iodide, potassium iodide and/or tetrabutylphosphonium iodide, in particular lithium chloride, ammonium chloride, dimethylammonium chloride, and/or diethanolammonium chloride.

It may be pointed out here that the presence of the ionic halide can be dispensed with and the process can be carried out, in particular, in the absence of the ionic halide.

It is possible to employ a palladium catalyst which contains palladium applied to a support material in the process. A palladium supported catalyst of this type has the advantage that it can be removed from the reaction mixture, for example by filtration, in a simple manner.

In a number of cases, it has proven suitable for the palladium catalyst to contain at least one palladium(II) compound, in particular $PdCl_2$, $PdBr_2$ or $Pd(OAc)_2$, preferably $PdCl_2$, or at least one palladium(0) compound, in particular $Pd_2dba_3$, in which dba is dibenzylideneacetone, $Pd(P(C_6H_5)_3)_4$ or $Pd(\eta^4—C_8H_{12})_2$, preferably $Pd_2dba_3$.

In a number of cases, it has furthermore proven favorable if the palladium catalyst additionally contains a ligand, in particular a phosphine compound. A suitable phosphine compound is, for example, a monophosphine, in particular a tri-($C_1$–$C_6$-alkyl)phosphine or a triarylphosphine, or a diphosphine. It is possible to good effect to employ triphenylphosphine, tritolylphosphine, bis(diphenylphosphino)ethane, 1,3-bis(diphenylphosphino)propane or 1,4-bis(diphenylphosphino)butane, in particular triphenylphosphine.

According to a preferred embodiment, the palladium catalyst contains a bis(triphenylphosphine)palladium(II) compound, for example bis(triphenylphosphine)-palladium (II) chloride or bis(triphenylphosphine)palladium(II) bromide.

The palladium catalyst is customarily employed corresponding to an amount of 0.00001 to 0.3 mol of palladium, in particular 0.000025 to 0.2 mol of palladium, preferably 0.00005 to 0.1 mol of palladium per mole of 1,2-bishalomethylbenzene.

In a large number of cases, it suffices to carry out the reaction at a CO pressure of 0.1 to 20 MPa, in particular 0.5 to 10, preferably 1.0 to 6, MPa.

Customarily, the reaction can be carried out to good effect at a temperature of 50 to 170° C., in particular 70 to 160° C., preferably 90 to 150° C.

As already mentioned at the outset, the reaction is carried out in the presence of a dipolar aprotic solvent. It is customarily sufficient to employ the dipolar aprotic solvent in an amount of 30 to 95, in particular 50 to 90, preferably 60 to 85, % by weight, based on the total mixture employed.

A suitable dipolar aprotic solvent is dioxane, tetrahydrofuran, an N—($C_1$–$C_{18}$-alkyl)pyrrolidone, ethylene glycol dimethyl ether, a $C_1$–$C_4$-alkyl ester of an aliphatic $C_1$–$C_6$-carboxylic acid, a $C_1$–$C_6$-dialkyl ether, an N,N-di-($C_1$–$C_4$-alkyl)amide of an aliphatic $C_1$–$C_4$-carboxylic acid, sulfolane, a 1,3-di-($C_1$–C8-alkyl)-2-imidazolidinone, an N—($C_1$–$C_8$-alkyl)caprolactam, an N,N,NN,NN-tetra-($C_1$–$C_8$-alkyl)urea, a 1,3-di-($C_1$–$C_8$alkyl)-3,4,5,6-tetrahydro-2(1H)-pyrimidone, an N,N,NN,NN-tetra-($C_1$–$C_8$-alkyl)sulfamide, 4-formylmorpholine, 1-formylpiperidine or 1-formylpyrrolidine, in particular an N—($C_1$–$C_{18}$-alkyl)pyrrolidone, an N,N-di-($C_1$–$C_4$-alkyl) amide of an aliphatic $C_1$–$C_4$-carboxylic acid, 4-formylmorpholine, 1-formylpiperidine or 1-formylpyrrolidine, preferably N-methylpyrrolidone, N-octylpyrrolidone, N-dodecylpyrrolidone, N,N-dimethylformamide, N,N-dimethylacetamide, 4-formylmorpholine, 1-formylpiperidine or 1-formylpyrrolidine, particularly preferably N-methylpyrrolidone, N, N-dimethylformamide or N,N-dimethylacetamide, very particularly preferably N-methylpyrrolidone. Mixtures of the abovementioned dipolar aprotic solvents can also be used.

As mentioned at the outset, the process is carried out with addition of water or without addition of water, in particular with addition of water. In many cases, an addition of water in minor amounts, for example 0.001 to 0.3 mol of water per mole of 1,2-bishalomethylbenzene of the formula (II), has proven favorable.

Customarily, the reaction is carried out with an amount of water corresponding to 0.005 to 0.25, in particular 0.01 to 0.1, preferably 0.02 to 0.08, mol of water per mole of 1,2-bishalomethylbenzene of the formula (II).

According to a particular embodiment of the process according to the invention, the 1,2-bishalomethylbenzene of the formula (II), the palladium catalyst, the dipolar aprotic solvent and, if appropriate, the ionic halide are initially introduced, the CO pressure and the temperature are adjusted and a mixture consisting of water and dipolar aprotic solvent and subsequently the compound of the formula (III) or a mixture consisting of the compound of the formula (III) and dipolar aprotic solvent are metered in.

During the reaction, provision is made for thorough mixing of the reactants in order to guarantee a rapid course of reaction.

The process according to the invention is suitable both for carrying out continuously and batchwise.

As a rule, the reaction is carried out at an $H_0$ value of $\leq 7$, in particular at $H_0 = -3$ to 7, preferably at $-2$ to 6. However, it is also possible to carry out the reaction at an $H_0$ value of $-1$ to 5, in particular at $-1$ to 4. The $H_0$ value, which is a measure of the acidity of a solvent and for which for dilute solutions $H_0$. pH, is described in Hollemann-Wiberg "Lehrbuch der Anorganischen Chemie" [Textbook of Inorganic Chemistry], 91–100th Edition, Verlag Walter de Gruyter, Berlin 1985, on pages 246–248. Kislina et al. describe, for example, the acidity of HCl in N,N-dimethylformamide in Russ. Chem. Bull., 1994, Vol. 43, on pages 960–963. As a rule, the appropriate $H_0$ value is established by itself in the course of a reaction, so that additional measures for the adjustment of the $H_0$ value are usually not necessary.

The $H_0$ value follows from the equation below:

$$H_0 = pK_{S,In} + \log C_{In}/C_{InH^+} \text{(Hammett's acidity function)}.$$

In this case, In is the indicator base and $InH^+$ the protonated form of the indicator base.

The following examples describe the invention, without restricting it.

EXPERIMENTAL SECTION

EXAMPLES

Example 1

Preparation of isochroman-3-one 299 g of 1,2-bischloromethylbenzene and 75 mg of palladium(II) chloride are dissolved in 725 g of N-methylpyrrolidone and mixed under a protective gas atmosphere (argon) in a 2000 ml autoclave made of HC 4 steel. Carbon monoxide is subsequently added at a pressure of 2 MPa and the temperature is increased to 150° C. At 150° C. and 2.5 MPa, 1.7 g of a mixture of water/N-methylpyrrolidone (weight ratio 1:1) is metered in in the course of 2 minutes and subsequently 415 g of a mixture of tert-butanol/N-methylpyrrolidone (weight ratio 2:1) is metered in in the course of 165 minutes. The reaction pressure is kept constant at 4 MPa during the addition. After the addition, the mixture is allowed to react for 60 minutes with stirring, and the autoclave is cooled and emptied.

1445 g of reaction mixture are obtained. Gas-chromatographic analysis shows that the reaction mixture contains 168 g of isochroman-3-one, corresponding to a yield of 66.4% of isochroman-3-one, based on 1,2-bischloromethylbenzene employed (TON=2649; TOF=706× $h^{-1}$).

Comparative Example 1

Preparation of isochroman-3-one without Addition of a Dipolar Aprotic Solvent 35.0 g of bischloromethylbenzene, 35 mg of palladium(II) chloride and 0.12 g of water are dissolved in 85 ml of tert-butanol and mixed under a protective gas atmosphere (argon) in a 300 ml autoclave made of HC 256 steel. Carbon monoxide at a pressure of 1.8 MPa is subsequently added and the temperature is increased to 100° C. No absorption of carbon monoxide is observed during the temperature increase and at the temperature of 100° C. Subsequently the temperature is slowly increased to 130° C.; carbon monoxide is also not absorbed in this case. At a pressure of 2.3 MPa, 35 mg of palladium(II) chloride dissolved in 5 ml of tert-butanol and 0.12 g of water are again metered in. No absorption of carbon monoxide is observed. A further addition of 2 ml of water/tert-butanol (1:1) likewise leads to no reaction.

After a further 2 hours, the autoclave is cooled and depressurized. Gaschromatographic analysis shows that the reaction mixture contains no 3-isochromanone.

Comparative Example 2

Preparation of isochroman-3-one with Addition of Calcium Hydroxide as a Hydrogen Halide Absorbent.

52.5 g of 1,2-bischloromethylbenzene, 1.05 g of bis(triphenylphosphine)palladium(II) chloride and 0.87 g of triphenylphosphine are mixed in 100 ml of tert-butanol and suspended in a 500 ml glass autoclave under a protective gas atmosphere (argon) with 48.0 g of water and 46.8 g of calcium hydroxide.

The temperature is subsequently increased to 70° C. under a carbon monoxide atmosphere. The carbon monoxide absorption begun with vigorous stirring at 60° C. is complete after 2 hours and a viscous magma is obtained. The addition of a further 1.05 g of bis(triphenylphosphine)palladium(II) chloride and 0.87 g of triphenylphosphine does not lead to any further absorption of carbon monoxide. After cooling, the mixture is acidified to pH 1 using hydrochloric acid and extracted with diethyl ether. 383 g of aqueous phase and 299 g of organic phase are obtained. According to gas-chromatographic analysis, the aqueous phase contains no isochroman-3-one, and according to gas-chromatographic analysis the organic phase contains 10.5 g of isochroman-3-one (Yield =24%; TON=46; TOF=15.4×$h^{-1}$).

What is claimed is:

1. A process for the preparation of an isochroman-3-one of the formula (I)

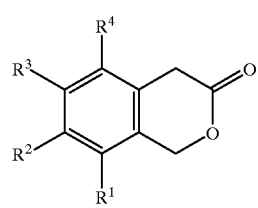

(I)

by reaction of a 1,2-bishalomethylbenzene of the formula (II)

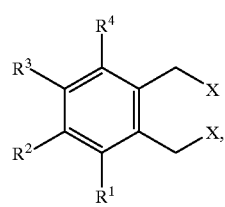

(II)

in which X is chlorine, bromine or iodine, with carbon monoxide and a compound of the formula (III)

$R^5R^6R^7C$—OH   (III)

at a CO pressure of 0.1 to 50 MPa and a temperature of 20 to 200° C. in the presence or absence of an ionic halide, in the presence of a palladium catalyst and of a dipolar aprotic solvent, with addition of water or without addition of water, where in the formulae (I) and (II) the radicals $R^1$, $R^2$, $R^3$ and $R^4$ independently of one another are:

a hydrogen or fluorine atom;

an NC or $F_3C$ group;

an alkyl, alkoxy or acyloxy radical, in each case having 1 to 18 carbon atoms; or a $C_6$–$C_{18}$-aryloxy, aryl or heteroaryl radical, where 1 to 3 atoms from the group consisting of O, N and/or S are present as heteroatoms;

or in which at least two of the radicals $R^1$, $R^2$, $R^3$ and $R^4$ are linked to one another and form at least one aliphatic or aromatic ring having 5 to 18 carbon atoms, and in formula (III) the radicals $R^5$, $R^6$ and $R^7$ are identical or different and are a $C_1$–$C_{18}$-alkyl, an HOC(=O)—, $H_3CC(=O)CH_2$— or ($C_6$–$C_{18}$-aryl)-$CH_2$— radical or at least two of the radicals $R^5$, $R^6$ and $R^7$ are linked to one another and form at least one aliphatic or aromatic ring having 5 to 18 carbon atoms.

2. The process as claimed in claim 1, wherein the radicals $R^1$, $R^2$, $R^3$ and $R^4$ independently of one another are hydrogen, fluorine, $C_1$–$C_4$-alkyl or $C_1$–$C_4$-alkoxy or two of the radicals $R^1$, $R^2$, $R^3$ and $R^4$ are linked to one another and form an aliphatic or aromatic ring having 5 to 10 carbon atoms.

3. The process as claimed in claim 1, wherein two, three or four of the radicals $R^1$, $R^2$, $R^3$ and $R^4$ are hydrogen.

4. The process as claimed in claim 1, wherein a compound of the formula (III) is employed in which $R^5$, $R^6$ and $R^7$ are identical or different and are a $C_1$–$C_8$-alkyl radical.

5. The process as claimed in claim 1, wherein a compound of the formula (III) is employed in which one of the radicals $R^5$, $R^6$ and $R^7$ is a $C_1$–$C_8$-alkyl radical and the remaining radicals are a methyl radical.

6. The process as claimed in claim 1, wherein tert-butanol is employed as the compound of the formula (III).

7. The process as claimed in claim 1, wherein the compound of the formula (III) is employed corresponding to an amount of 0.8 to 10 mol per mole of 1,2-bishalomethylbenzene of the formula (II).

8. The process as claimed in claim 1, wherein the ionic halide is an alkali metal, ammonium or phosphonium halide, where halide has the meaning chloride, bromide or iodide.

9. The process as claimed in claim 1, wherein the palladium catalyst contains metallic palladium or at least one palladium(II) compound or at least one palladium(0) compound applied to a support material.

10. The process as claimed in claim 1, wherein the palladium catalyst contains a phosphine compound in addition as a ligand.

11. The process as claimed in claim 9, wherein the phosphine compound is triphenylphosphine, tritolylphosphine, bis(diphenylphosphino)ethane, 1,3-bis(diphenylphosphino)propane or 1,4-bis(diphenylphosphino)butane.

12. The process as claimed in claim 1, wherein the palladium catalyst is bis(triphenylphosphine)palladium(II) chloride or bis(triphenylphosphine)palladium(II) bromide.

13. The process as claimed in claim 1, wherein the palladium catalyst is employed corresponding to an amount of 0.00001 to 0.3 mol of palladium per mole of 1,2-bishalomethylbenzene.

14. The process as claimed in claim 1, wherein the dipolar aprotic solvent is dioxane, tetrahydrofuran, an N—($C_1$–$C_{18}$-alkyl)pyrrolidone, ethylene glycol dimethyl ether, a $C_1$–$C_4$-alkyl ester of an aliphatic $C_1$–$C_6$-carboxylic acid, a $C_1$–$C_6$-dialkyl ether, an N,N-di-($C_1$–$C_4$-alkyl)amide of an aliphatic $C_1$–$C_4$-carboxylic acid, sulfolane, a 1,3-di-($C_1$–$C_8$-alkyl)-2-imidazolidinone, an N—($C_1$–$C_8$-alkyl)caprolactam, an N,N,N',N'-tetra-($C_1$–$C_8$-alkyl)urea, a 1,3-di-($C_1$–$C_8$-alkyl)-3,4,5,6-tetrahydro-2(1H)-pyrimidone, an N,N,N',N'-tetra-($C_1$–$C_8$-alkyl)sulfamide, 4-formylmorpholine, 1-formylpiperidine or 1-formylpyrrolidine.

15. The process as claimed in claim 1, wherein the dipolar aprotic solvent is N-methylpyrrolidone, N-octylpyrrolidone, N-dodecylpyrrolidone, N,N-dimethylformamide, N,N-dimethylacetamide, 4-formylmorpholine, 1-formylpiperidine or 1-formylpyrrolidine.

16. The process as claimed in claim 1, wherein water is employed corresponding to an amount of 0.005 to 0.25 mol per mole of 1,2-bishalomethylbenzene of the formula (II).

* * * * *